(12) United States Patent
Schafer et al.

(10) Patent No.: US 11,317,875 B2
(45) Date of Patent: May 3, 2022

(54) RECONSTRUCTION OF FLOW DATA

(71) Applicant: Siemens Healthcare GmbH, Erlangen (DE)

(72) Inventors: Sebastian Schafer, Madison, WI (US); Sonja Gehrisch, Nuremberg (DE); Markus Kowarschik, Nuremberg (DE); Christopher Rohkohl, Hattingen (DE); Kevin Royalty, Fitchburg, WI (US)

(73) Assignee: Siemens Healthcare GmbH, Erlangen (DE)

( * ) Notice: Subject to any disclaimer, the term of this patent is extended or adjusted under 35 U.S.C. 154(b) by 274 days.

(21) Appl. No.: 15/710,724

(22) Filed: Sep. 20, 2017

(65) Prior Publication Data

US 2018/0092608 A1 Apr. 5, 2018

(30) Foreign Application Priority Data

Sep. 30, 2016 (EP) ..................... 16191701

(51) Int. Cl.
*A61B 6/03* (2006.01)
*A61B 6/00* (2006.01)
(Continued)

(52) U.S. Cl.
CPC .............. *A61B 6/032* (2013.01); *A61B 6/037* (2013.01); *A61B 6/481* (2013.01); *A61B 6/486* (2013.01);
(Continued)

(58) Field of Classification Search
CPC ....... A61B 6/032; A61B 6/507; A61B 6/5288; A61B 6/504; A61B 6/5205; A61B 6/486;
(Continued)

(56) References Cited

U.S. PATENT DOCUMENTS 5,522,393 A * 6/1996 Phillips .................... A61B 8/06
600/455
6,246,898 B1 * 6/2001 Vesely ..................... A61B 5/06
600/424
(Continued)

FOREIGN PATENT DOCUMENTS

CN 1620991 A 6/2005
CN 102696056 A 9/2012
(Continued)

OTHER PUBLICATIONS

B. Davis, K. Royalty, M. Kowarschik, C. Rohkohl, E. Oberstar, B. Aagaard-Kienitz, D. Niemann, O. Ozkan, C. Strother and C. Mistretta, 4D Digital Subtraction Angiography: Implementation and Demons, American Journal of Neuroradiology, 34 (10) 1914-1921; DOI: https://doi.org/10.3174/ajnr.A3529 (Year: 2013).*
(Continued)

*Primary Examiner* — Amanda Lauritzen Moher
*Assistant Examiner* — Amy J Shafqat

(57) ABSTRACT

Described herein are technologies for facilitating reconstruction of flow data. In accordance with one aspect, the framework receives a four-dimensional projection image dataset and registers one or more pairs of temporally adjacent projection images in the image dataset. Two-dimensional flow maps may be determined based on the registered pairs. The framework may then sort the two-dimensional flow maps according to heart phases, and reconstruct a three-dimensional flow map based on the sorted two-dimensional flow maps.

18 Claims, 8 Drawing Sheets

(51) Int. Cl.
*G06T 7/00* (2017.01)
*G06T 11/00* (2006.01)
(52) U.S. Cl.
CPC ............. *A61B 6/504* (2013.01); *A61B 6/507* (2013.01); *A61B 6/5205* (2013.01); *A61B 6/5288* (2013.01); *G06T 7/0016* (2013.01); *G06T 11/006* (2013.01); *G06T 11/008* (2013.01); *A61B 6/501* (2013.01); *A61B 6/503* (2013.01); *A61B 6/5235* (2013.01); *G06T 11/003* (2013.01); *G06T 2200/04* (2013.01); *G06T 2207/10016* (2013.01); *G06T 2207/10116* (2013.01); *G06T 2207/30104* (2013.01); *G06T 2211/412* (2013.01); *G06T 2211/432* (2013.01)

(58) Field of Classification Search
CPC ......... A61B 6/481; A61B 6/037; A61B 6/503; A61B 6/5235; A61B 6/5001; G06T 7/0016; G06T 11/008; G06T 11/006; G06T 2207/10016; G06T 2207/10116; G06T 11/003; G06T 2207/30104; G06T 2211/432; G06T 2211/412; G06T 2200/04; G06T 2207/30101; G06T 2211/436; G06T 2211/404; G06T 2211/424; G06T 11/005; G06T 7/38
See application file for complete search history.

(56) References Cited

U.S. PATENT DOCUMENTS

| | | | | |
|---|---|---|---|---|
| 6,447,450 | B1* | 9/2002 | Olstad | A61B 5/0456 600/437 |
| 6,503,202 | B1* | 1/2003 | Hossack | A61B 8/06 600/454 |
| 8,073,224 | B2* | 12/2011 | Strobel | A61B 6/469 382/130 |
| 8,463,007 | B2* | 6/2013 | Steinberg | A61B 6/501 382/128 |
| 8,463,012 | B2* | 6/2013 | Rauch | G06T 7/38 382/130 |
| 8,771,189 | B2* | 7/2014 | Ionasec | G06T 7/262 600/437 |
| 8,929,632 | B2* | 1/2015 | Horz | A61B 6/504 382/130 |
| 9,443,330 | B2 | 9/2016 | Heigl | |
| 9,508,157 | B2* | 11/2016 | Schafer | G06T 7/0012 |
| 9,684,980 | B2* | 6/2017 | Royalty | G06T 19/00 |
| 9,754,390 | B2* | 9/2017 | Heigl | G06T 11/008 |
| 10,271,905 | B2* | 4/2019 | Ashikaga | A61B 34/10 |
| 2005/0259864 | A1* | 11/2005 | Dickinson | G06K 9/00134 382/154 |
| 2006/0140482 | A1* | 6/2006 | Koehler | G06T 11/006 382/193 |
| 2008/0205726 | A1* | 8/2008 | Boese | G06T 19/00 382/130 |
| 2009/0161938 | A1* | 6/2009 | Shekhar | A61B 8/483 382/131 |
| 2010/0208962 | A1* | 8/2010 | Roessl | G06T 11/005 382/131 |
| 2010/0240996 | A1* | 9/2010 | Ionasec | G06T 7/0016 600/443 |
| 2010/0259550 | A1* | 10/2010 | Baumgart | A61B 6/481 345/589 |
| 2010/0295846 | A1* | 11/2010 | Schaefer | G06T 11/006 345/419 |
| 2011/0235885 | A1* | 9/2011 | Rauch | A61B 6/4441 382/131 |
| 2011/0299749 | A1* | 12/2011 | Rauch | G06T 7/254 382/130 |
| 2012/0114217 | A1* | 5/2012 | Mistretta | A61B 6/4441 382/133 |
| 2012/0150048 | A1* | 6/2012 | Kang | G06T 7/149 600/481 |
| 2013/0094745 | A1* | 4/2013 | Sundar | G06T 3/0068 382/132 |
| 2013/0129172 | A1 | 5/2013 | Boese et al. | |
| 2014/0071125 | A1* | 3/2014 | Burlina | G06T 17/00 345/420 |
| 2014/0121513 | A1* | 5/2014 | Tolkowsky | A61B 5/02007 600/431 |
| 2014/0376791 | A1* | 12/2014 | Heigl | G06T 11/008 382/128 |
| 2015/0094584 | A1* | 4/2015 | Abe | A61B 8/5223 600/443 |
| 2016/0135775 | A1* | 5/2016 | Mistretta | A61B 6/5247 600/411 |
| 2016/0140730 | A1* | 5/2016 | Falahatpisheh | G01S 15/89 382/131 |
| 2016/0203288 | A1* | 7/2016 | Meng | G06T 7/60 703/2 |
| 2016/0239958 | A1 | 8/2016 | Bannae et al. | |
| 2016/0267704 | A1 | 9/2016 | Mistretta et al. | |
| 2016/0278725 | A1 | 9/2016 | Van Nijnatten | |
| 2017/0055931 | A1* | 3/2017 | Paysan | A61B 6/032 |
| 2018/0253854 | A1* | 9/2018 | Falahatpisheh | A61B 8/466 |

FOREIGN PATENT DOCUMENTS

| | | |
|---|---|---|
| CN | 104252714 A | 12/2014 |
| JP | 2008173236 A | 7/2008 |
| JP | 2009519082 A | 5/2009 |
| JP | 2009279290 A | 12/2009 |
| JP | 2014528333 A | 10/2014 |
| JP | 2016146995 A | 8/2016 |
| WO | 2012011014 | 1/2012 |

OTHER PUBLICATIONS

Nicolas Passat, Christian Ronse, Joseph Baruthio, Jean-Paul Armspach, Claude Maillot. Magnetic resonance angiography: From anatomical knowledge modeling to vessel segmentation. Medical Image Analysis, Elsevier, 2006, 10 (2), pp. 259-274. ff10.1016/j.media.2005.11.002ff. ffhal-01694419f (Year: 2006).*
Office Action dated Sep. 4, 2018, received in corresponding Japanese Application No. 2017-186408, with translation.
A. Chien, et al., "IS FlowMap, a novel tool to examine blood flow changes induced by flow diverter stent treatment: Initial experiences with pipeline cases," J. Neurointerv. Surg 2013, p. 1-5.
A.D. Copeland, et al., "Spatio-temporal Data Fusion for 3D+T Image Reconstruction in Cerebral Angiography", Medical Imaging, IEEE Transactions 2010, vol. 29, No. 6, pp. 1238-1251.
C.A. Mistretta, "Sub-Nyquist acquisition and constrained reconstruction in time resolved angiography", Medical Physics 2011, vol. 38, No. 6, pp. 2975-2985.
I. Waechter, et al., "Model-based blood flow quantification from rotational angiography", Medical Image Analysis 2008, vol. 12, pp. 586-602.
V.M. Pereira, et al., "A DSA-based Method Using Contrast-Motion Estimation for the Assessment of the Intra-Aneurysmal Flow Changes Induced by Flow-Diverter Stents", American Jounral of Neuroradiology, vol. 34, No. 4, Nov. 2, 2012, pp. 808-815.
EP Search Report dated Mar. 31, 2017 from counterpart EP application No. 16191701.8, 9 pages total.

* cited by examiner

US 11,317,875 B2

RECONSTRUCTION OF FLOW DATA

RELATED CASE

This application claims the benefit of European Patent Office Application Serial No. 16191701.8 filed on Sep. 30, 2016, which is hereby incorporated by reference in its entirety.

TECHNICAL FIELD

The present disclosure relates generally to automated or partially-automated reconstruction of flow data.

BACKGROUND

Angiography is a common method used to represent blood vessels based on diagnostic imaging methods. For an improved representation of the vessels under X-ray examination, Digital Subtraction Angiography (DSA) has been developed. DSA is an X-ray technique used in interventional radiology to clearly visualize vasculature in a bony or dense soft tissue environment. Images are produced by subtracting a "pre-contrast image" or the mask from subsequent images after the contrast agent has been introduced into a structure or tissue of interest. These images can be used to provide time-resolved or time-varying information that shows movement of the structure or tissue of interest over time.

Deriving flow information from angiographic images has been an object of interest for a considerable time. Current technology makes use of two-dimensional (2D) DSA images acquired with a static C-Arm position at a high frame rate time series across a series of heart phases. Most methods then use the optical flow approach to derive vectors indicating the magnitude and direction of the contrast change from frame to frame. While 2D methods have been widely discussed, they are challenged with overlapping vasculature and typically fail in the presence of implants.

SUMMARY

A technology for facilitating reconstruction of flow data is described herein. In accordance with one aspect, the framework receives a four-dimensional projection image dataset and registers one or more pairs of temporally adjacent projection images in the image dataset. Two-dimensional flow (2D) maps may be determined based on the registered pairs. Each pixel of the 2D flow maps may comprise a first flow vector representing a flow magnitude and a two-dimensional flow direction (u', v'). The framework may then sort the 2D flow maps according to heart phases, and reconstruct a three-dimensional (3D) flow map based on the sorted flow maps. Each voxel in the 3D flow map may comprise a flow vector that represents a flow magnitude and a 3D flow direction (x', y', z').

This summary is provided to introduce a selection of concepts in a simplified form that are further described below in the following detailed description. It is not intended to identify features or essential features of the claimed subject matter, nor is it intended that it be used to limit the scope of the claimed subject matter. Furthermore, the claimed subject matter is not limited to implementations that solve any or all disadvantages noted in any part of this disclosure.

BRIEF DESCRIPTION OF THE DRAWINGS

A more complete appreciation of the present disclosure and many of the attendant aspects thereof will be readily obtained as the same becomes better understood by reference to the following detailed description when considered in connection with the accompanying drawings. Furthermore, it should be noted that the same numbers are used throughout the drawings to reference like elements and features.

DETAILED DESCRIPTION

Figure 1:
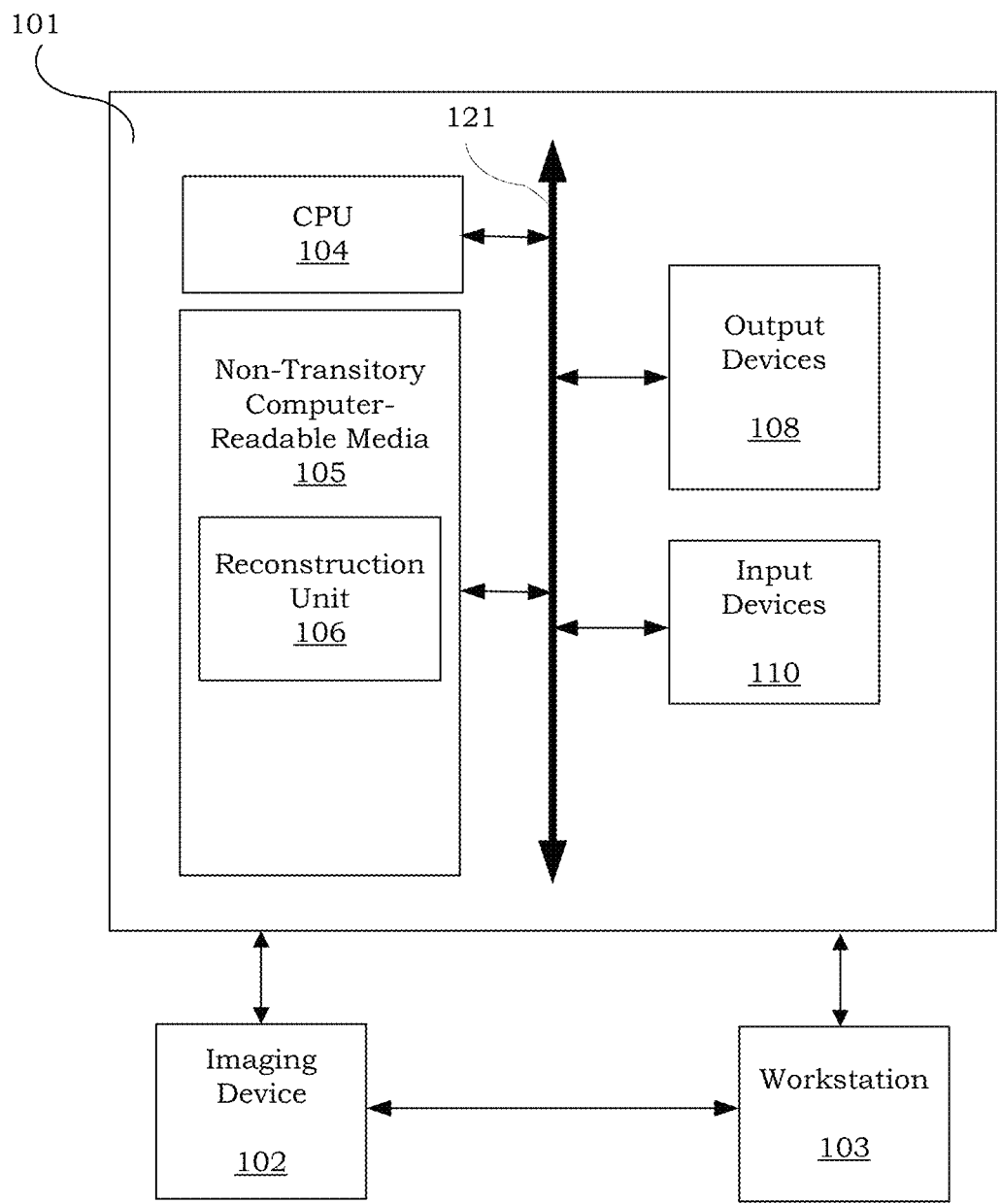
FIG. 1 is a block diagram illustrating an exemplary imaging system.

In the following description, numerous specific details are set forth such as examples of specific components, devices, methods, etc., in order to provide a thorough understanding of embodiments of the present invention. It will be apparent, however, to one skilled in the art that these specific details need not be employed to practice embodiments of the present invention. In other instances, well-known materials or methods have not been described in detail in order to avoid unnecessarily obscuring embodiments of the present invention. While the invention is susceptible to various modifications and alternative forms, specific embodiments thereof are shown by way of example in the drawings and will herein be described in detail. It should be understood, however, that there is no intent to limit the invention to the particular forms disclosed, but on the contrary, the invention is to cover all modifications, equivalents, and alternatives falling within the spirit and scope of the invention.

The term "x-ray image" as used herein may mean a visible x-ray image (e.g., displayed on a video screen) or a digital representation of an x-ray image (e.g., a file corresponding to the pixel output of an x-ray detector). The term "in-treatment x-ray image" as used herein may refer to images captured at any point in time during a treatment delivery phase of any interventional procedure, which may include times when the radiation source is either on or off. From time to time, for convenience of description, cone-beam CT (CBCT) imaging data may be used herein as an exemplary imaging modality. It will be appreciated, however, that data from any type of imaging modality including but not limited to X-Ray radiographs, MRI, CT, PET (positron emission tomography), PET-CT, SPECT, SPECT-CT, MR-PET, 3D ultrasound images or the like may also be used in various embodiments of the invention.

Unless stated otherwise as apparent from the following discussion, it will be appreciated that terms such as "segmenting," "generating," "registering," "determining," "aligning," "positioning," "processing," "computing," "selecting," "estimating," "detecting," "tracking" or the like may refer to the actions and processes of a computer system, or similar electronic computing device, that manipulate and transform data represented as physical (e.g., electronic)

quantities within the computer system's registers and memories into other data similarly represented as physical quantities within the computer system's memories or registers or other such information storage, transmission or display devices. Embodiments of the methods described herein may be implemented using computer software. If written in a programming language conforming to a recognized standard, sequences of instructions designed to implement the methods can be compiled for execution on a variety of hardware platforms and for interface to a variety of operating systems. In addition, embodiments of the present invention are not described with reference to any particular programming language. It will be appreciated that a variety of programming languages may be used to implement embodiments of the present invention.

As used herein, the term "image" or "image data" refers to multi-dimensional data composed of discrete image elements (e.g., pixels for 2D images and voxels for 3D images). The image may be, for example, a medical image of a subject collected by (cone-beam) computed tomography, magnetic resonance imaging, ultrasound, or any other medical imaging system known to one of skill in the art. The image may also be provided from non-medical contexts, such as, for example, remote sensing systems, electron microscopy, etc. Although an image can be thought of as a function from $R^2$ to $R^4$ or $R^{8t}$ the methods of the inventions are not limited to such images, and can be applied to images of any dimension, e.g., a 2D picture or a 3D volume. For a 2- or 3-dimensional image, the domain of the image is typically a 2- or 3-dimensional rectangular array, wherein each pixel or voxel can be addressed with reference to a set of 2 or 3 mutually orthogonal axes. The terms "digital" and "digitized" as used herein will refer to images or volumes, as appropriate, in a digital or digitized format acquired via a digital acquisition system or via conversion from an analog image.

To alleviate the problems encountered by traditional 2D methods, the present framework acquires DSA data in a rotational fashion that generates a time-varying 3D representation of blood/contrast mixture flow direction. In its typical form, such 4D-DSA data is used only as a qualitative tool for visual inspection. Nevertheless, the incorporated contrast dynamics allow for assessing quantitative metrics, such as the direction of the contrast/blood flow mixture for a given heart phase.

Traditional methods for deriving 2D flow vectors typically use the approach of optical flow, incorporating both the spatial contrast change in a projection view and the contrast change in between temporal frames, resulting in a 2D flow vector for each projection image pixel. Applied as it is, this method will fail due to the angular difference between projection frames (up to 1.5 degrees) in rotational acquisitions.

To incorporate 3D flow vector visualization from rotationally acquired projection images, the flow vectors from 2D subsequent projection frames may first be quantified prior to phase-binned reconstruction. One aspect of the present framework generates heart phase-specific contrast/blood mixture 3D flow maps from an existing 4D-DSA dataset. Each voxel in the 3D flow map may comprise a flow vector that represents 3D flow direction (x', y', z') and a magnitude of the flow. Temporally adjacent projection images in the 4D-DSA dataset are first registered to account for the angular difference. Projection-based flow calculation may then be performed to determine flow vectors between the registered projection images. A 3D flow map may be reconstructed based on the flow vectors. These and other exemplary features and advantages will be described in more details herein.

FIG. 1 is a block diagram illustrating an exemplary imaging system 100. The imaging system 100 includes a computer system 101 for implementing the framework as described herein. The computer system 101 may be further connected to an imaging device 102 and a workstation 103, over a wired or wireless network. The imaging device 102 may be a radiology scanner such as a magnetic resonance (MR) scanner, X-ray or a CT scanner. In some implementations, imaging device 102 employs cone-beam CT (or C-arm CT, cone beam volume CT, flat panel CT, etc.) imaging technologies to acquire a volumetric or 3D dataset reconstructed from different views of the patient's anatomy or structure of interest. The imaging device 102 may include a scanner mounted on, for example, a C-arm that rotates around the patient's body to acquire distinct images representing multiple views. Different implementations of the imaging device 102 may include, for example, fixed-room C-arm, mobile U-arm, mobile O-arm, mobile C-arm, and so forth.

Computer system 101 may be a desktop personal computer, a portable laptop computer, another portable device, a mini-computer, a mainframe computer, a server, a storage system, a dedicated digital appliance, or another device having a storage sub-system configured to store a collection of digital data items. In one implementation, computer system 101 comprises a processor or central processing unit (CPU) 104 coupled to one or more non-transitory computer-readable media 105 (e.g., computer storage or memory), output devices 108 (e.g., monitor, display, printer, etc.) and various input devices 110 (e.g., mouse, keyboard, touch pad, voice recognition module, etc.) via an input-output interface 121. Computer system 101 may further include support circuits such as a cache, a power supply, clock circuits and a communications bus. Even further, computer system 101 may be provided with a graphics controller chip, such as a graphics processing unit (GPU) that supports high performance graphics functions.

It is to be understood that the present technology may be implemented in various forms of hardware, software, firmware, special purpose processors, or a combination thereof. In one implementation, the techniques described herein are implemented by reconstruction unit 106. Reconstruction unit 106 may include computer-readable program code tangibly embodied in non-transitory computer-readable media 105. Non-transitory computer-readable media 105 may include random access memory (RAM), read only memory (ROM), magnetic floppy disk, flash memory, and other types of memories, or a combination thereof. The computer-readable program code is executed by CPU 104 to control and/or process image data from imaging device 102.

As such, the computer system 101 is a general-purpose computer system that becomes a specific-purpose computer system when executing the computer readable program code. The computer-readable program code is not intended to be limited to any particular programming language and implementation thereof. It will be appreciated that a variety of programming languages and coding thereof may be used to implement the teachings of the disclosure contained herein. Computer system 101 may also include an operating system and microinstruction code. The various techniques described herein may be implemented either as part of the microinstruction code or as part of an application program or software product, or a combination thereof, which is executed via the operating system. Various other peripheral devices, such as additional data storage devices and printing devices, may be connected to the computer system 101.

The workstation 103 may include a computer and appropriate peripherals, such as a keyboard and display, and can be operated in conjunction with the entire system 100. For example, the workstation 103 may communicate with the imaging device 102 so that the image data collected by the imaging device 102 can be rendered at the workstation 103 and viewed on the display. The workstation 103 may include a user interface that allows a radiologist or any other skilled user (e.g., physician, technician, operator, scientist, etc.), to manipulate the image data. For example, a user may identify structures or regions of interest in the image data, or annotate the structures or regions of interest using pre-defined descriptors via the user interface. Further, the workstation 103 may communicate directly with computer system 101 to display processed or reconstructed image data. For example, a radiologist can interactively manipulate the displayed representation of the processed image data and view it from various viewpoints and in various reading modes.

Figure 2:
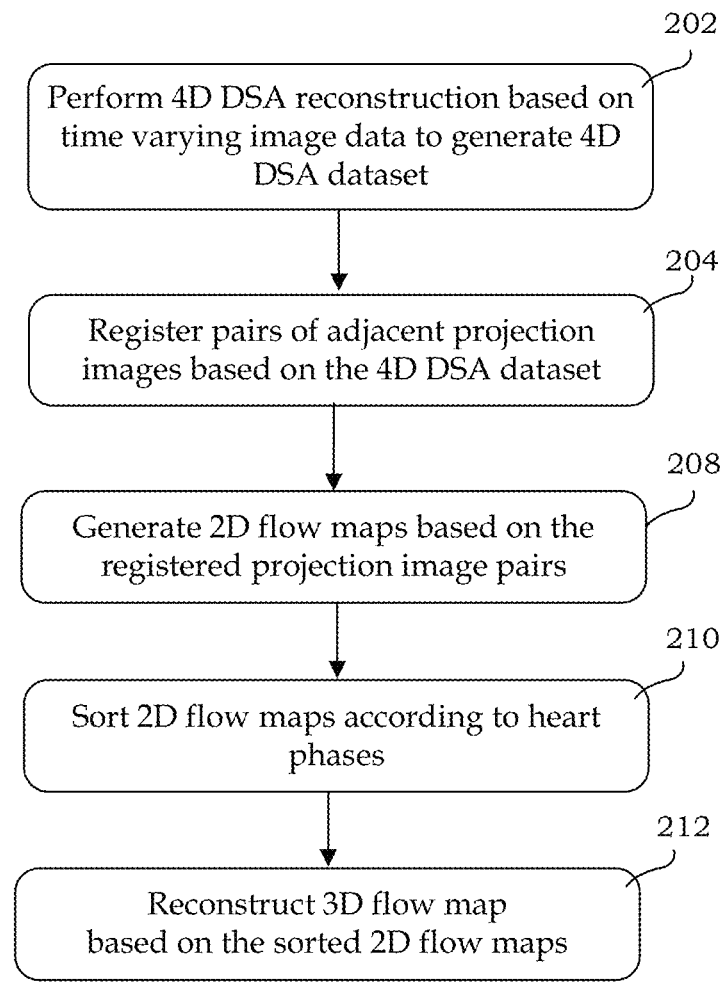
FIG. 2 shows an exemplary method of reconstructing flow data.

FIG. 2 shows an exemplary method 200 of reconstructing flow data. The exemplary method 200 may be implemented by the reconstruction unit 106 in computer system 101, previously described with reference to FIG. 1. It should be noted that in the following discussion, reference will be made, using like numerals, to the features described in FIG. 1.

At 202, reconstruction unit 106 performs 4D DSA reconstruction based on time-varying image data to generate a 4D (or time-resolved 3D) DSA dataset V4D of an object of interest. The 4D DSA dataset V4D represents phase information of injected contrast flow or dynamics in vessel-like structures of the object of interest. The 4D DSA dataset V4D may include a time series of 3D angiographic image volumes that allows viewing of a contrast bolus passing through the vessel-like structures at any time during its passage, and at any desired viewing (or projection) angle. A set of time-contrast concentration (TCC) curves may be extracted from the 4D DSA dataset V4D. Each TCC curve provides information on contrast density, and in turn heart phase, for a given image element (e.g. pixel for 2D data, voxel for 3D volume), and is generated by re-projecting individual projection images into the volumetric domain.

The object of interest may be any biological object identified for investigation or examination, such as a portion of a patient's or subject's brain, heart, leg, arm, and so forth. The object of interest includes one or more vessel-like structures (e.g., blood vessels, arteries, vascular tree or network, etc.). The one or more vessel-like structures may be dynamic or time-varying structures that can be filled with a contrast agent or medium for observing its propagation over time. In some implementations, a static (i.e., non-temporal) 3D image data of a device (e.g., flow diverting device) implanted in the object of interest is also reconstructed.

The time-varying image data may be a set of digitized 2D DSA projection images that are acquired by performing a rotational scan or angular acquisitions using imaging device 102. A sequence of subtracted projection images may be acquired with an X-ray delay via the imaging device 102 to capture as many heart phases with opacification as possible. More particularly, a mask image dataset may first be acquired via the imaging device 102 such that it can be subtracted from the corresponding time-varying contrast filled projection image dataset. A mask image is simply an image of the same area before the contrast agent (or medium) is administered to fill the vessel-like structures of the irradiated object of interest that is to be investigated. The actual angular- and time-varying 2D projection data may be based on a contrast enhanced acquisition that is initiated before or after the injection of contrast medium into the vessel-like structures as the first inflow of contrast becomes visible. Both mask and fill runs may follow the same acquisition trajectory. The trajectory may cover the entire field-of-view (FOV) range of a 3D DSA.

Imaging device 102 may be a scanner or C-arm system with a single, dual or multiple imaging planes. For example, imaging device 102 may be a flat-panel based X-ray scanner that includes at least one pair of X-ray source and X-ray detector. Alternatively, imaging device 102 may include a rotating CT gantry covering at least one pair of X-ray source and X-ray detector. In other implementations, imaging device 102 is an MR projection scanner. In yet other implementations, imaging device 102 is a rotating optical CT gantry covering at least one pair of light source and optical detector. Other types of imaging device 102, such as angular sampling ultrasound, may also be used. A single image may be acquired at each angular position. Alternatively, two images with a temporal delay are acquired at each angular position, so as to avoid having to perform subsequent image registration.

Methods for performing a 4D-DSA reconstruction of time-varying image data acquired by a single rotating plane C-arm system are described in U.S. application Ser. No. 14/302,596 filed on Jun. 12, 2014 (now U.S. Pub. No. 2014/0376791), which is hereby incorporated by reference. These methods determine time-varying volumetric attenuation curves of the vessel-like structures, resulting in a 3D plus time (or 4D-DSA) volumetric dataset that includes the time dimension. The 4D-DSA dataset may also be derived from time-varying and projection-angle-varying data. Confidence values or curves may be used in performing interpolation of time-resolved 3D DSA. Such framework may be applied once, or in an iterative fashion. The 4D-DSA dataset may also be dynamically and iteratively reconstructed based on, for example, an initial time-varying 3D projection dataset derived from time-varying 2D projection data acquired at multiple angles.

Methods for performing a 4D-DSA reconstruction of time-varying image data acquired by a dual C-arm system are described in German application no. 102015224176.9 filed on Dec. 3, 2015 entitled "Tomography system and method for generating a sequence of volume images of a vasculature" (also PCT application no. PCT/EP2015/079102 filed on Dec. 9, 2015), which are hereby incorporated by reference. These techniques are based on an angiographic biplane system that comprises two simultaneously rotating planes. The accuracy of the reconstructed series of time-resolved volumes can be significantly improved, since information from the two planes can be exploited to mitigate accuracy issues due to vascular overlap.

Returning to FIG. 2, at 204, reconstruction unit 106 registers pairs of temporally adjacent (or subsequently acquired) rotational projection images based on the 4D DSA image data. Each pair of temporally adjacent projection images may be denoted by $P_t$ and $P_{t+1}$. To perform the registration, reconstruction unit 106 may first identify the V4D volumes ($V4D_t$ and $V4D_{t+1}$) corresponding to each projection image pair $P_t$ and $P_{t+1}$. Next, reconstruction unit 106 may register the projection image $P_t$ with projection image $P_{t+1}$ by determining the projection displacement from known system geometries associated with the projection images. More particularly, for each projection image, there exists an acquisition geometry G (source and detector positions) that uniquely describes the system. For two adjacent projection images $P_t$ and $P_{t+1}$ and their respective system geometries $G_t$ and $G_{t+1}$, a deformation field may be derived to register a volume V4D$_{t+1}$ with the volume V4D$_t$. This deformation field D(t+1 ▶ t) may then be forward projected into projection image $P_{t+1}$ to generate a 2D projection displacement (or deformation vector field) d(t+1 ▶ t). Such projection displacement may be applied to projection image $P_t$ to generate registered projection image $P_{t+1}$P$_{t+1 \blacktriangleright t}$.

Figure 3:
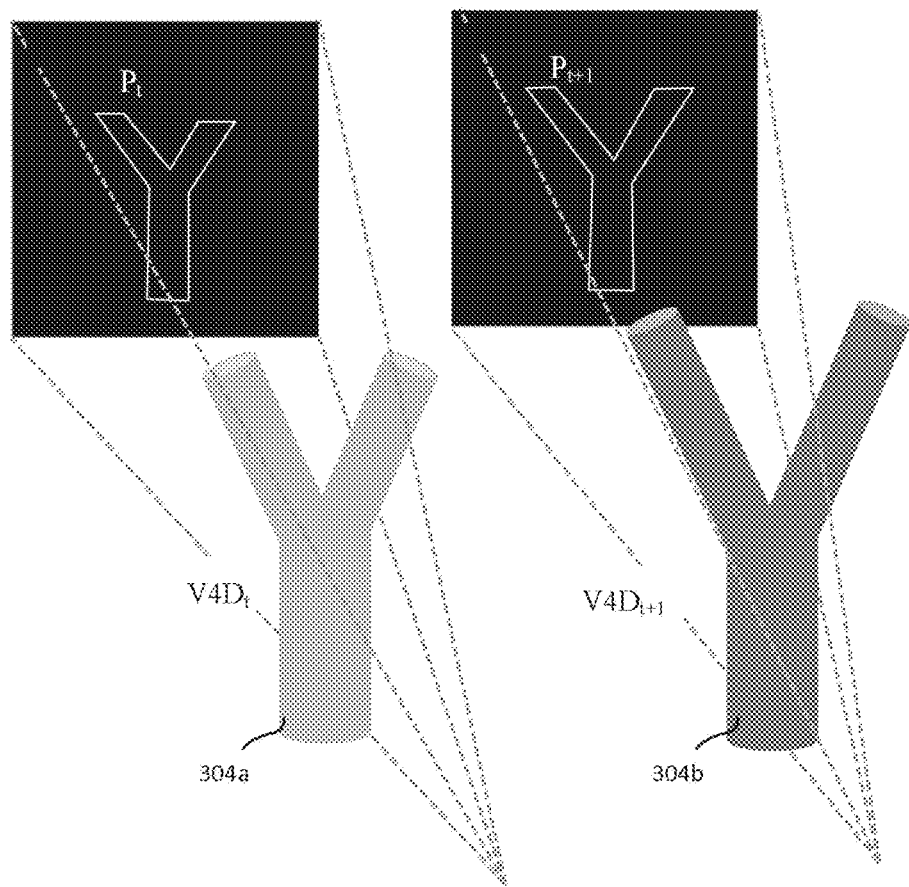
FIG. 3 shows projection images $P_t$ and $P_{t+1}$ at two subsequent time points.
Figure 4:
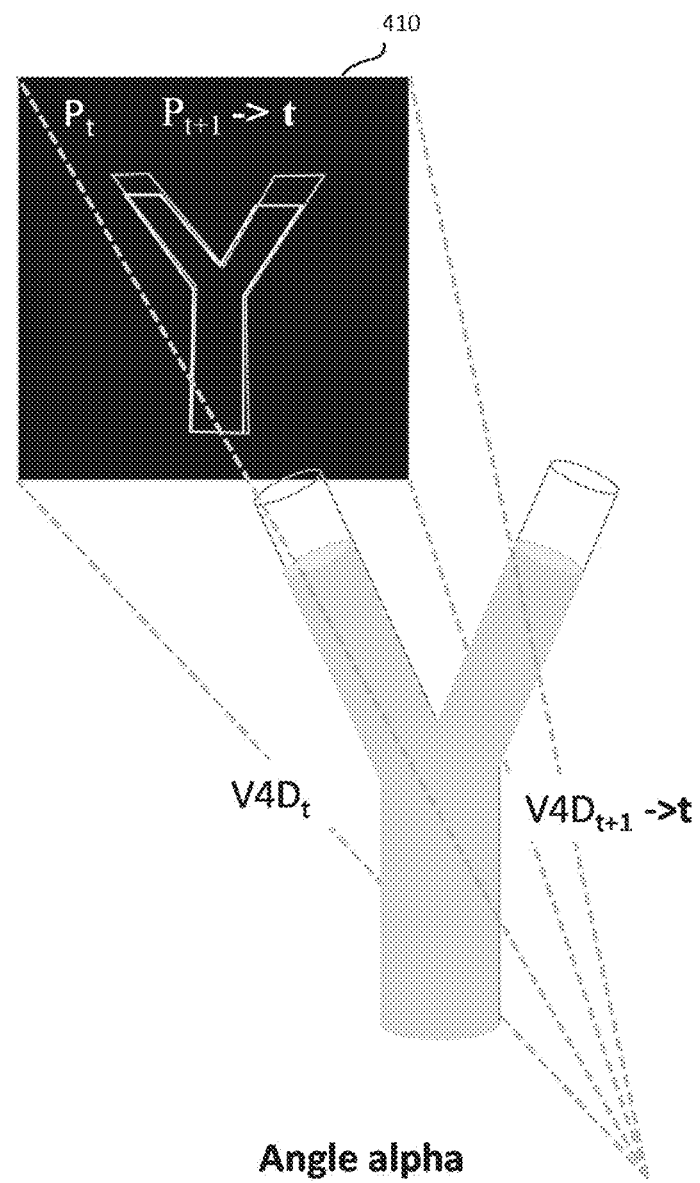
FIG. 4 shows the volume $V4D_{t+1}$ after it has been registered to volume $V4D_t$.

Alternatively, reconstruction unit 106 may register the adjacent rotational projection images $P_t$ and $P_{t+1}$ by forward projecting V4D$_{t+1}$ using the acquisition geometry of V4D$_t$ to create a registered image $P_{t+1}$P$_{t+1 \blacktriangleright t}$. This exemplary method is illustrated by FIGS. 3-4. FIG. 3 shows projection images $P_t$ and $P_{t+1}$ at two subsequent time points (t and t+1) with a small angular increment between them. The contrast agent has progressed between acquisitions, as is visible by the different fill states of the structure 304a-b as captured by volumes V4D$_t$ and V4D$_{t+1}$. FIG. 4 shows the volume V4D$_{t+1}$ after it has been registered (or translated) to volume V4D$_t$. Forward projection of the volume V4D$_{t+1}$→t using the acquisition geometry of V4D$_t$ results in the registered projection image pair 410 ($P_t$ and $P_{t+1}$→t). T registration matrices may be generated by incorporating the change in contrast from each volume through a frame-by-frame projection method.

At 208, reconstruction unit 106 generates 2D flow maps based on the adjacent registered projection images. Each pixel of the 2D flow map represents a flow vector at a particular 2D position (u, v) of the projection image. N projection images corresponding to different projection angles may be processed to generate T 2D flow maps, wherein T=N−1 since 2 projection images are used to compute a flow map. Each flow vector represents the 2D direction (u', v') of a contrast flow between the registered projection images $P_t$ and $P_{t+1}$, as well as the magnitude of the contrast flow. Such flow vectors may be determined by using projection-based flow calculation methods (e.g., optical flow).

At 210, reconstruction unit 106 sorts the 2D flow maps according to heart phases. The sorting may be performed using an electrocardiography (ECG) trace signal, or the underlying time-contrast concentration (TCC) curves derived from the 4D DSA dataset itself. More particularly, ECG gating or TCC distribution of the processed projection data (flow vectors established) may be used to sort the 2D flow maps into phase bins. The sorting may result in N phase bins containing M radially-distributed flow maps.

Figure 5:
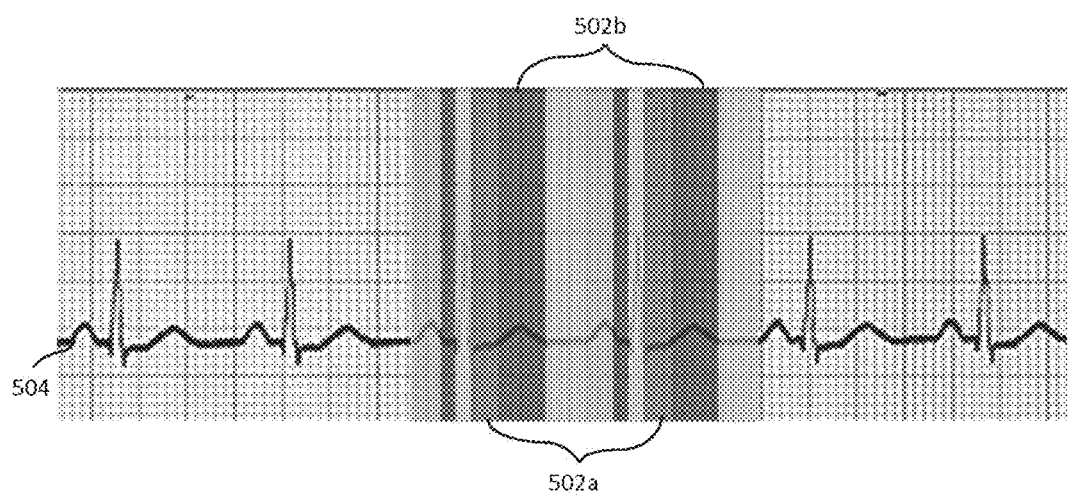
FIG. 5 illustrates how an electrocardiography (ECG) trace signal is used for sorting 2D flow maps into phase bins.
Figure 6:
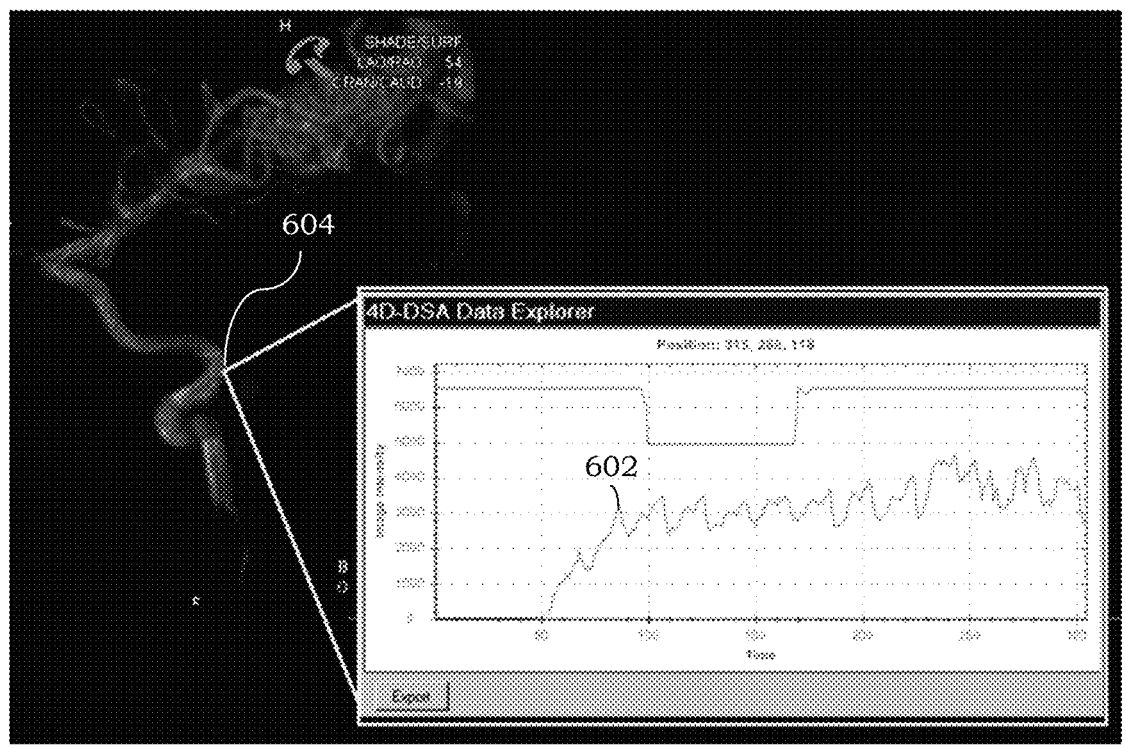
FIG. 6 shows an exemplary time-contrast concentration (TCC) curves discernable at the root of the internal carotid artery.
Figure 7:
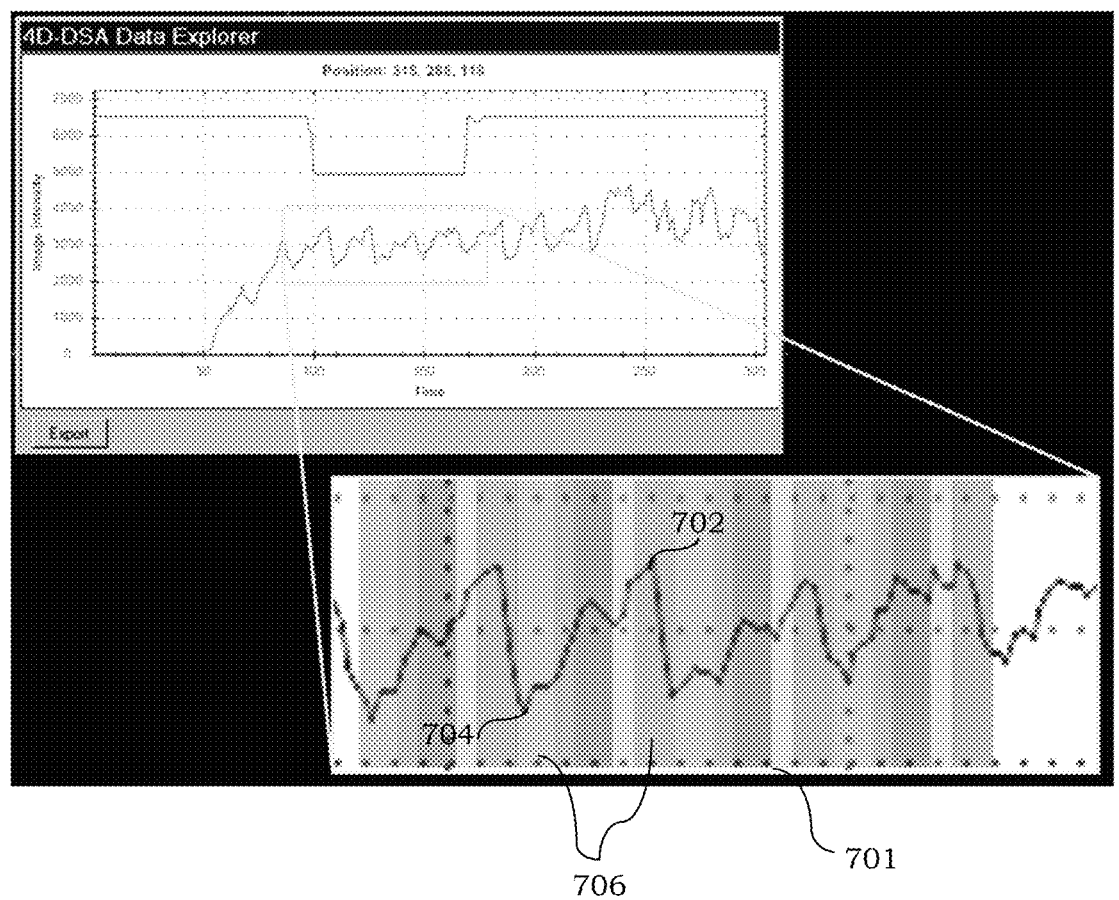
FIG. 7 is a schematic diagram of phase binning performed based on four-dimensional (4D) DSA data.

FIG. 5 illustrates how an ECG trace signal 504 is used for sorting 2D flow maps into phase bins 502a-b. Each set of vertically shaded areas (e.g., 502a or 502b) represents a phase bin corresponding to a particular phase of the ECG trace signal. FIG. 6 shows an exemplary TCC 602 discernable at the root of the internal carotid artery 604 that may be used for sorting the 2D flow maps. TCC 602 represents concentration/image intensities over time and may be extracted from the 4D-DSA dataset. TCC 602 may be used alone or in combination with information determined from the ECG signal monitoring to provide further input for projection image sorting. FIG. 7 is a schematic diagram 701 of phase binning performed based on 4D DSA data. Time-contrast concentration (TCC) curve peaks 702 correspond to diastole, while valleys 704 correspond to systole. During systole, non-opacified blood is flowing into the vasculature, thinning the contrast agent and resulting in a lower attenuation of incident x-rays. The 2D flow maps may be sorted into phase bins 706 using heart phases indicated by the TCC.

Returning to FIG. 2, at 212, reconstruction unit 106 generates a 3D flow map based on the sorted 2D flow maps. Each voxel of the 3D flow map represents one or more 3D flow vectors at a particular 3D position (x, y, z) and heart phase. Each 3D flow vector represents a particular flow magnitude and 3D flow direction (x', y', z'). The 3D flow map may be displayed at, for example, workstation 103. Such 3D flow map may be used to present a detailed pattern of flow changes for assessing and/or diagnosing diseases, such as arterial stenosis or aneurysm inflow.

To generate the 3D flow map, 2D flow maps in each heart phase bin may be separately and tomographically reconstructed to yield an estimated distribution of the flow vectors in 3D space. Tomographic reconstruction generally involves backprojecting 2D projection images that are independent of intensity or flow data into 3D space by taking system geometries into consideration. See, for example, Feldkamp, et al., *Practical cone-beam algorithm*, J. Opt. Soc. Am., Vol 1, 1984, pages 1612-619, which is herein incorporated by reference. In some implementations, tomographic reconstruction is performed by using simple backprojection of the flow vectors in the 2D flow maps and accumulating the flow vectors in three-dimensional space.

Figure 8:
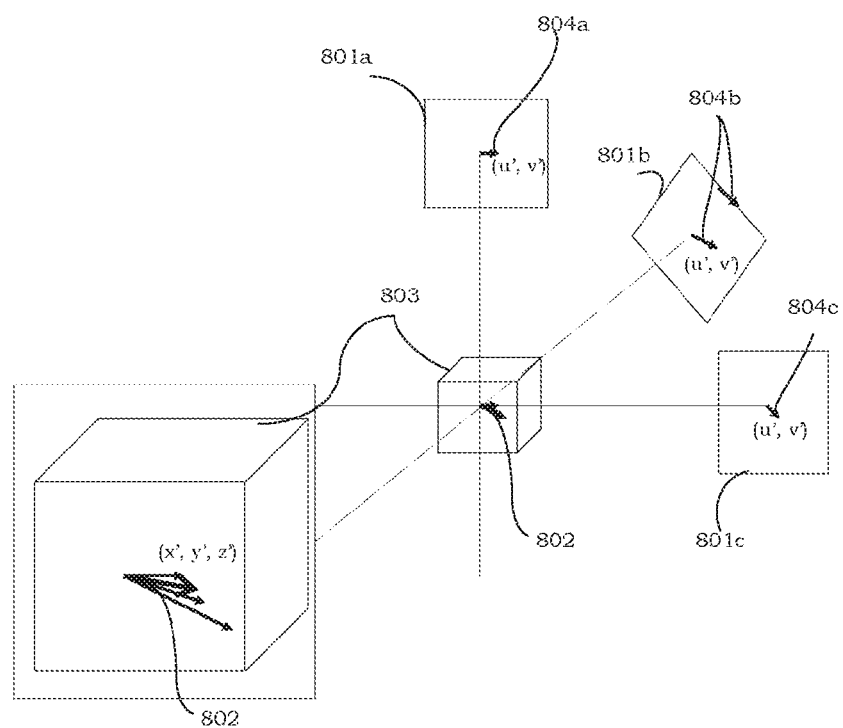
FIG. 8 illustrates an exemplary tomographic reconstruction technique.

FIG. 8 illustrates an exemplary tomographic reconstruction technique. Each 2D projection map 801a-c is associated with a (u, v) space, while the 3D image 803 is associated with an (x, y, z) space. 2D flow vectors 804a-c may be extracted from 2D flow maps grouped in a particular heart phase bin. 3D flow vectors 802 may be obtained by backprojecting and algebraically combining the flow vectors 804a-c. While each 2D flow vector 804a-c in the projection domain only has the two directional components (u', v') and a flow magnitude value for a particular pixel (u, v) in 2D space, backprojecting these 2D flow vectors from different angular positions corresponding to a particular heart phase bin results in a 3D flow vector 802 with three directional components (x', y', z') and flow magnitude values for a particular voxel (x, y, z) in 3D space.

In summary, the system acquisition geometry establishes the relationship between a 2D projection map (801a-c) and a 3D volume 803. The backprojected information has multiple directional components (u, v, u', v') and magnitude values. Each map may be backprojected separately to achieve three different volumes that can be combined to yield the final directional (x', y', z') and magnitude values.

To further improve flow map reconstruction, smoothness of the flow may be enforced by using a regularizer on the reconstructed 3D flow map. Reconstruction of 3D flow map and regularizer may be implemented by an iterative optimization framework. More particularly, the optimization framework may alternate between optimizing the fit of the reconstructed flow map to the derived 2D flow maps and applying a smoothing regularizer between adjacent flow phases. The optimization may be performed on a user-defined sub-region of the 3D flow map, which allows for faster computation.

Although the one or more above-described implementations have been described in language specific to structural features and/or methodological steps, it is to be understood that other implementations may be practiced without the specific features or steps described. Rather, the specific features and steps are disclosed as preferred forms of one or more implementations.

The invention claimed is:

1. A non-transitory computer readable medium embodying a program of instructions executable by machine to perform steps comprising:
   receiving an existing four-dimensional digital subtraction angiography (DSA) dataset;
   registering pairs of temporally adjacent projection images derived from corresponding four-dimensional image volumes that are identified from the existing four-dimensional DSA dataset to generate registered pairs of temporally adjacent projection images;
   determining two-dimensional flow maps based on the registered pairs of temporally adjacent projection images, wherein a pixel of the two-dimensional flow maps comprises a first flow vector of a plurality of flow vectors of a contrast agent representing a first flow magnitude and a two-dimensional flow direction of the contrast agent between two temporally adjacent projection images in at least one of the registered pairs of temporally adjacent projection images;
   sorting the two-dimensional flow maps according to heart phases to generate sorted two-dimensional flow maps; and
   reconstructing a three-dimensional flow map by backprojecting the plurality of flow vectors in the sorted two-dimensional flow maps and algebraically combining the flow vectors in a three-dimensional space, wherein a voxel of the reconstructed three-dimensional flow map comprises a three-dimensional flow vector of the contrast agent representing a second flow magnitude and a three-dimensional flow direction of the contrast agent.

2. The non-transitory computer readable medium of claim 1 wherein the instructions are executable by the machine to perform the sorting the two-dimensional flow maps according to the heart phases to generate the sorted two-dimensional flow maps by using an electrocardiography (ECG) trace signal.

3. The non-transitory computer readable medium of claim 1 wherein the instructions are executable by the machine to perform the sorting the two-dimensional flow maps according to the heart phases to generate the sorted two-dimensional flow maps by using time-contrast concentration (TCC) curves derived from the existing four-dimensional DSA dataset.

4. A method of reconstructing flow data, comprising:
   receiving an existing four-dimensional projection image dataset;
   registering pairs of temporally adjacent projection images derived from corresponding four-dimensional image volumes that are identified from the existing four-dimensional projection image dataset to generate registered pairs of temporally adjacent projection images;
   determining two-dimensional flow maps of a contrast agent based on the registered pairs of temporally adjacent projection images;
   sorting the two-dimensional flow maps of the contrast agent according to heart phases to generate sorted two-dimensional flow maps of the contrast agent; and
   reconstructing a three-dimensional flow map of the contrast agent by backprojecting flow vectors in the sorted two-dimensional flow maps and algebraically combining the flow vectors in a three-dimensional space.

5. The method of claim 4, further comprises reconstructing the existing four-dimensional projection image dataset based on two-dimensional time-varying image data.

6. The method of claim 5 further comprises acquiring, by an imaging device, the two-dimensional time-varying image data by acquiring a single image at each angular position.

7. The method of claim 5 further comprises acquiring, by an imaging device, the two-dimensional time-varying image data by acquiring two images with a temporal delay at each angular position.

8. The method of claim 4 wherein registering the pairs of temporally adjacent projection images comprises:
   determining a projection displacement based on the corresponding four-dimensional image volumes and based on system geometries associated with at least one of the pairs of temporally adjacent projection images; and
   applying the projection displacement to one image of the at least one of the pairs of temporally adjacent projection images to generate a registered projection image.

9. The method of claim 4 wherein registering the pairs of temporally adjacent projection images derived from the corresponding four-dimensional image volumes that are identified from the existing four-dimensional projection image dataset comprises:
   forward projecting a first image volume of the corresponding four-dimensional image volumes using an acquisition geometry of a second image volume of the corresponding four-dimensional image volumes to generate a registered projection image.

10. The method of claim 4 wherein determining the two-dimensional flow maps of the contrast agent comprises determining said flow vectors by using a projection-based flow calculation method.

11. The method of claim 4 wherein sorting the two-dimensional flow maps of the contrast agent according to the heart phases comprises sorting the two-dimensional flow maps of the contrast agent using an electrocardiography (ECG) trace signal.

12. The method of claim 4 wherein sorting the two-dimensional flow maps of the contrast agent according to the heart phases comprises sorting the two-dimensional flow maps of the contrast agent using time-contrast concentration (TCC) curves derived from the existing four-dimensional projection image dataset.

13. The method of claim 4 wherein reconstructing the three-dimensional flow map of the contrast agent comprises separately and tomographically reconstructing the sorted two-dimensional flow maps of the contrast agent in at least one of the heart phases.

14. The method of claim 4 further comprises applying a regularizer on the reconstructed three-dimensional flow map of the contrast agent.

15. The method of claim 14 wherein applying the regularizer comprises applying the regularizer on a user-defined sub-region of the reconstructed three-dimensional flow map of the contrast agent.

16. A system, comprising:
   a non-transitory memory device for storing computer readable program code; and
   a processor in communication with the memory device, the processor is operative with the computer readable program code to perform operations including
   receive an existing four-dimensional projection image dataset,
   register pairs of temporally adjacent projection images derived from corresponding four-dimensional image volumes that are identified from the existing four-dimensional projection image dataset to generate registered pairs of temporally adjacent projection images, determine two-dimensional flow maps of a contrast agent based on the registered pairs of temporally adjacent projection images, sort the two-dimensional flow maps of the contrast agent according to heart phases to generate sorted two-dimensional flow maps of the contrast agent, and reconstruct a three-dimensional flow map of the contrast agent by backprojecting flow vectors in the sorted two-dimensional flow maps and algebraically combining the flow vectors in a three-dimensional space.

17. The system of claim 16 wherein the processor is operative with the computer readable program code to perform the sorting the two-dimensional flow maps of the contrast agent according to the heart phases to generate the sorted two-dimensional flow maps of the contrast agent by using an electrocardiography (ECG) trace signal.

18. The system of claim 16 wherein the processor is operative with the computer readable program code to perform the sorting the two-dimensional flow maps of the contrast agent according to the heart phases to generate the sorted two-dimensional flow maps of the contrast agent by using time-contrast concentration (TCC) curves derived from the existing four-dimensional projection image dataset.

* * * * *

UNITED STATES PATENT AND TRADEMARK OFFICE
CERTIFICATE OF CORRECTION

PATENT NO. : 11,317,875 B2
APPLICATION NO. : 15/710724
DATED : May 3, 2022
INVENTOR(S) : Sebastian Schafer et al.

Page 1 of 1

It is certified that error appears in the above-identified patent and that said Letters Patent is hereby corrected as shown below:

In the Claims

Column 11, Claim 17, Line 15 "... perform the sorting the two-dimensional flows maps..." should read "... perform the sorting of the two-dimensional flow maps..."

Column 11, Claim 18, Line 21 "... perform the sorting the two-dimensional flows maps..." should read "... perform the sorting of the two-dimensional flow maps..."

Signed and Sealed this
Twenty-seventh Day of September, 2022

Katherine Kelly Vidal
*Director of the United States Patent and Trademark Office*